United States Patent
Yamazaki et al.

(10) Patent No.: US 6,316,628 B1
(45) Date of Patent: Nov. 13, 2001

(54) L-TARTRATE OF TRANS-(-)-4-(4-FLUOROPHENYL)-3-HYDROXYMETHYLPIPERIDINE COMPOUND AND PROCESS FOR PREPARING THE SAME

(75) Inventors: Shigeya Yamazaki; Taro Ishibashi; Yoshihiro Kawada; Hiroyuki Yumoto; Taichi Yoshikawa; Masami Igi, all of Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/342,149

(22) Filed: Jun. 29, 1999

(30) Foreign Application Priority Data

Jun. 29, 1998 (JP) ................................................. 10-182766

(51) Int. Cl.[7] ................................................. C07D 211/22
(52) U.S. Cl. ................................................. 546/240
(58) Field of Search ................................................. 546/240

(56) References Cited

U.S. PATENT DOCUMENTS

| | | | |
|---|---|---|---|
| 4,007,196 | 2/1977 | Christensen et al. | 546/197 |
| 5,948,914 | * 9/1999 | Sugi et al. | 546/240 |

FOREIGN PATENT DOCUMENTS

| | | |
|---|---|---|
| 0223334A1 | 5/1987 | (EP) . |
| 0802185A1 | 10/1997 | (EP) . |
| 0812827A1 | 12/1997 | (EP) . |
| 9403428 | 2/1994 | (WO) . |

OTHER PUBLICATIONS

Montzka et al. "Substituted tartranilic acids . . . " J. Org. chem. v. 33, p. 3993–5, 1968.*
Jacques et al. "Enantiomers, racemates and resolutions" Krieger Pub. p. 259–260, 1994.*
Nass et al. "Rational solvent selection for cooling crystallizations" CA 120:326130 (1994).
Rico et al. "N–methylsydnone a new solvent for molecular aggregation" CA 119:434789 (1992).
Pavia et al. "Introduction to organic laboratory techniques . . . " Saunders Publ. p. 481–489, 1988.*
Heterocyles, 109:6427k, p. 609 (1988).
English language abstract of JP–A–9–278754.

* cited by examiner

*Primary Examiner*—Ceila Chang
(74) *Attorney, Agent, or Firm*—Birch, Stewart, Kolasch & Birch, LLP

(57) ABSTRACT

An L-tartrate of a trans-(−)-4-(4-fluorophenyl)-3-hydroxymethylpiperidine compound, represented by the formula (I):

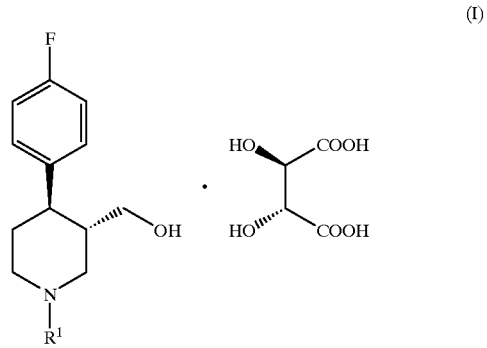

wherein R[1] is hydrogen atom, a substituted or unsubstituted, linear or branched alkyl group having 1 to 6 carbon atoms, or an aralkyl group having 7 to 12 carbon atoms. The L-tartrate of trans-(−)-4-(4-fluorophenyl)-3-hydroxymethylpiperidine compound can be suitably used as an intermediate for pharmaceuticals such as paroxetine which is useful, for example, as an antidepressant.

5 Claims, 4 Drawing Sheets

L-TARTRATE OF TRANS-(−)-4-(4-FLUOROPHENYL)-3-HYDROXYMETHYLPIPERIDINE COMPOUND AND PROCESS FOR PREPARING THE SAME

BACKGROUND OF THE INVENTION

1. Field of the Invention

The present invention relates to an L-tartrate of a trans-(−)-4-(4-fluorophenyl)-3-hydroxymethylpiperidine compound, and a process for preparing the same. More specifically, the present invention relates to an L-tartrate of a trans-(−)-4-(4-fluorophenyl)-3-hydroxymethylpiperidine compound which is useful as an intermediate for pharmaceuticals such as paroxetine which is useful, for example, as an antidepressant, and a process for preparing the same.

2. Discussion of the Related Art

Conventionally, a salt of tartranilic acid derivative of a trans-(−)-4-(4-fluorophenyl)-3-hydroxymethylpiperidine compound, represented by the formula (III):

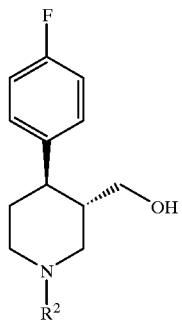

(III)

wherein $R^2$ is hydrogen atom, methyl group or benzyl group, has been prepared by optically resolving a trans-(±)-4-(4-fluorophenyl)-3-hydroxymethylpiperidine compound represented by the formula (IV):

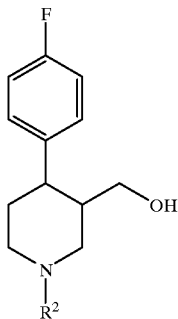

(IV)

wherein $R^2$ is the same as defined above, with a tartranilic acid derivative, such as (+)-2'-nitrotartranilic acid or (+)-2'-chlorotartranilic acid, as an optically resolving agent.

However, since the tartranilic acid derivative used as an optically resolving agent is extremely expensive, there is a defect in this process that a complicated procedure of collecting the tartranilic acid derivative after its use and purifying it for reuse is necessitated.

In addition, since the salt of tartranilic acid of the resulting trans-(−)-4-(4-fluorophenyl)-3-hydroxymethylpiperidine compound prepared by using the optically resolving agent has a low bulk density of 230 g/l or so, there arises a defect of poor production efficiency.

In view of the above problems, an object of the present invention is to provide a compound capable of being suitably used as an intermediate for pharmaceuticals such as paroxetine which is useful, for example, as an antidepressant, and a process for preparing the compound using an inexpensive optically resolving agent with high production efficiency.

These and other objects of the present invention will be apparent from the following description.

SUMMARY OF THE INVENTION

The present invention pertains to:

[1] an L-tartrate of a trans-(−)-4-(4-fluorophenyl)-3-hydroxymethylpiperidine compound, represented by the formula (I):

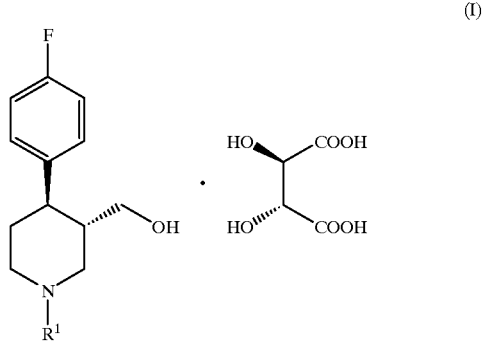

(I)

wherein $R^1$ is hydrogen atom, a substituted or unsubstituted, linear or branched alkyl group having 1 to 6 carbon atoms, or an aralkyl group having 7 to 12 carbon atoms; and

[2] a process for preparing a trans-(−)-4-(4-fluorophenyl)-3-hydroxymethylpiperidine compound, represented by the formula (I), comprising reacting a trans-(±)-4-(4-fluorophenyl)-3-hydroxymethylpiperidine compound represented by the formula (II):

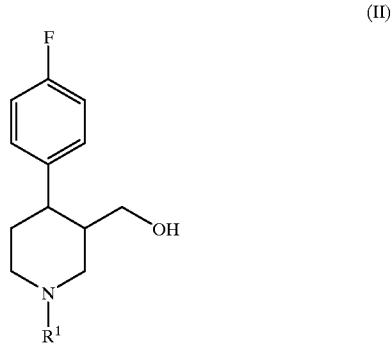

(II)

wherein $R^1$ is the same as defined above, with L-tartaric acid.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

DETAILED DESCRIPTION OF THE INVENTION

Figure 1:
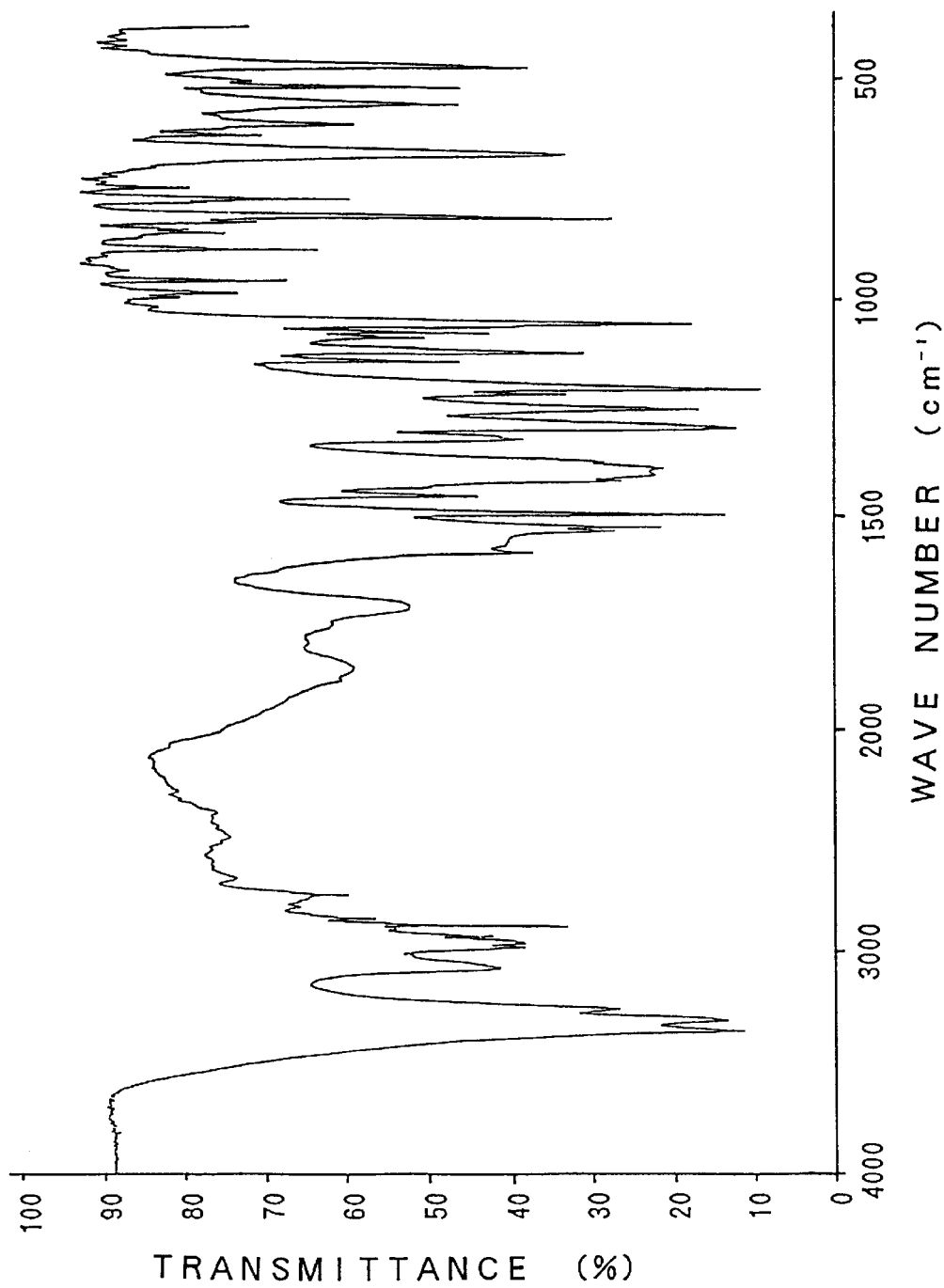
FIG. 1 is a chart showing an infrared absorption spectrum of the L-tartrate of trans-(−)-4-(4-fluorophenyl)-3-hydroxymethylpiperidine prepared in Reference Example.

The L-tartrate of a trans-(−)-4-(4-fluorophenyl)-3-hydroxymethylpiperidine compound of the present invention represented by the formula (I):

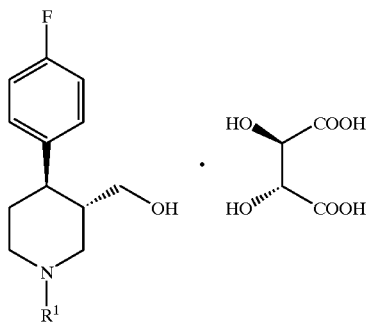

(I)

wherein $R^1$ is hydrogen atom, a substituted or unsubstituted, linear or branched alkyl group having 1 to 6 carbon atoms, or an aralkyl group having 7 to 12 carbon atoms, is a novel compound.

In the formula (I), $R^1$ is hydrogen atom, a substituted or unsubstituted, linear or branched alkyl group having 1 to 6 carbon atoms, or an aralkyl group having 7 to 12 carbon atoms.

The linear or branched alkyl group having 1 to 6 carbon atoms includes, for instance, linear alkyl groups having 1 to 6 carbon atoms, such as methyl group, ethyl group, n-propyl group, n-butyl group, n-pentyl group and n-hexyl group; branched alkyl groups having 3 to 6 carbon atoms, such as isopropyl group, sec-butyl group and tert-butyl group, and the like. Among $R^1$ mentioned above, hydrogen atom and methyl group are preferable.

The aralkyl group of 7 to 12 carbon atoms having a linear or branched alkyl group includes, for instance, benzyl group, and the like.

Incidentally, the alkyl group and the aralkyl group may have a substituent. The substituent includes, for instance, a halogen atom, methoxy group, an alkoxycarbonyl group having 2 to 8 carbon atoms.

The L-tartrate of a trans-(−)-4-(4-fluorophenyl)-3-hydroxymethylpiperidine compound, represented by the formula (I) can be prepared by reacting a trans-(±)-4-(4-fluorophenyl)-3-hydroxymethylpiperidine compound represented by the formula (II):

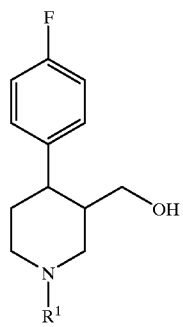

(II)

wherein $R^1$ is the same as defined above, with L-tartaric acid to form a salt.

One of the major features in the present invention resides in the use of L-tartaric acid as an optically resolving agent. Since the L-tartaric acid is an inexpensive and readily available compound, there are advantageous merits not only that the process of the present invention has excellent productivity on an industrial scale, but also that an L-tartrate of a trans-(−)-4-(4-fluorophenyl)-3-hydroxymethylpiperidine compound, having an extremely high bulk density of 650 to 700 g/l or so can be efficiently prepared. Moreover, when the L-tartaric acid is used, there can be exhibited an excellent effect that the amount of the solvent used during the formation of a salt can be dramatically reduced as compared to a case where conventional optically resolving agents such as a tartranilic acid derivative are used.

As described above, according to the process of the present invention, numerous remarkably excellent effects can be exhibited by using L-tartaric acid as an optically resolving agent, thereby enjoying remarkably excellent productivity on an industrial scale.

The trans-(±)-4-(4-fluorophenyl)-3-hydroxymethylpiperidine compound represented by the formula (II), is readily available from processes as disclosed, for instance, in Japanese Examined Patent Publication No. Hei 6-96551 and Japanese Patent Laid-Open No. Hei 9-278754.

When the trans-(±)-4-(4-fluorophenyl)-3-hydroxymethylpiperidine compound represented by the formula (II) is reacted with L-tartaric acid, a solvent can be used. The solvent includes, for instance, monohydric alcohols having 1 to 4 carbon atoms, such as methanol, ethanol, isopropanol; ketones, such as acetone and methyl ethyl ketone, and the like. Those solvents can be used alone or in an admixture thereof. Among them, a solvent comprising methanol as a main component is desirable from the viewpoint of obtaining trans-(−)-4-(4-fluorophenyl)-3-hydroxymethylpiperidine compound having high optical purity. In the present specification, the solvent comprising methanol as a main component refers to a solvent containing at least 50% by volume of methanol. Among the solvents comprising methanol as a main component, methanol or a mixed solvent of methanol and at least one compound of isopropyl alcohol and acetone is desirable from the viewpoint of obtaining trans-(−)-4-(4-fluorophenyl)-3-hydroxymethylpiperidine compound having higher optical purity. Also, the mixed solvent of methanol and at least one compound of isopropyl alcohol and acetone is also desirable from the viewpoint of obtaining trans-(−)-4-(4-fluorophenyl)- 3-hydroxymethylpiperidine compound in high yields. It is desired that the ratio of methanol to at least one compound of isopropyl alcohol and acetone is such that the amount of at least one compound of isopropyl alcohol and acetone is at least 10 parts by volume, preferably at least 20 parts by volume, more preferably at least 30 parts by volume, based on 100 parts by volume of methanol; from the viewpoint of obtaining the L-tartrate of a trans-(-)-4-(4-fluorophenyl)-3-hydroxymethylpiperidine compound in high yields. In addition, the ratio of methanol to at least one compound of isopropyl alcohol and acetone cannot be absolutely determined, because the optical purity of the resulting trans-(-)-4-(4-fluorophenyl)-3-hydroxymethylpiperidine compound may differ depending upon several factors such as amount of the solvent, temperatures during the formation of a salt, and period of time required for the formation of a salt as well as the ratio of methanol to at least one compound of isopropyl alcohol and acetone. Generally, in accordance with the increase of the ratio of methanol to at least one compound of isopropyl alcohol and acetone, its optical purity tends to be lowered. Accordingly, it is desired that the amount of at least one compound of isopropyl alcohol and acetone is usually at most 500 parts by volume, preferably at most 200 parts by volume, more preferably at most 100 parts by volume, further preferably at most 60 parts by volume, particularly preferably at most 40 parts by volume, based on 100 parts by volume of methanol, from the viewpoint of improvement in optical purity.

It is desired that the amount of the solvent is at least 200 parts by weight, preferably at least 500 parts by weight, based on 100 parts by weight of the trans-(±)-4-(4-fluorophenyl)-3-hydroxymethylpiperidine compound, from the viewpoint of giving an L-tartrate of a trans-(-)-4-(4-fluorophenyl)-3-hydroxymethylpiperidine compound with high optical purity, and that the amount of the solvent is at most 2000 parts by weight, preferably at most 700 parts by weight, based on 100 parts by weight of the trans-(±)-4-(4-fluorophenyl)-3-hydroxymethylpiperidine compound, from the viewpoint of improvement in yields.

When the trans-(±)-4-(4-fluorophenyl)-3-hydroxymethylpiperidine compound is reacted with L-tartaric acid to form a salt in a solvent, any of the trans-(±)-4-(4-fluorophenyl)-3-hydroxymethylpiperidine compound and L-tartaric acid can be firstly dissolved in the solvent.

It is desired that the amount of L-tartaric acid is at least 0.8 mol, preferably at least 0.9 mol, per one mol of the trans-(±)-4-(4-fluorophenyl)- 3-hydroxymethylpiperidine compound, from the viewpoint of giving a compound with high optical purity, and that the amount of L-tartaric acid is at most 2 mol, preferably at most 1.2 mol, per one mol of the trans-(±)-4-(4-fluorophenyl)-3-hydroxymethylpiperidine compound, from the viewpoint of suppression of the residual L-tartaric acid and economic advantages.

It is desired that the temperature during the formation of a salt is at least 0° C., preferably at least 10° C., more preferably at least 20° C., from the viewpoint of acceleration of the formation of a salt, and that the temperature is at most a boiling point of the solvent used, preferably at most 40° C. Particularly, it is desired that the temperature during the formation of a salt is 20° to 35° C., from the viewpoint of giving a L-tartrate of a trans-(-)-4-(4-fluorophenyl)-3-hydroxymethylpiperidine compound having high optical purity in high yields.

The atmosphere the formation of a salt is not limited to specified ones, and it may be air, or an inert gas such as nitrogen gas.

The time period required for the formation of a salt cannot be absolutely determined, because it may differ depending upon the conditions for the formation of a salt. Usually, the time period for the reaction is 1 to 24 hours or so. However, since the time period for the reaction is longer, the optical purity of the resulting L-tartrate of a trans-(-)-4-(4-fluorophenyl)-3-hydroxymethylpiperidine compound tends to be lowered, it is desired that the time period is as short as possible, for instance, at most 5 hours, preferably at most 3 hours.

Thus, the L-tartrate of a trans-(-)-4-(4-fluorophenyl)-3-hydroxymethylpiperidine compound can be precipitated as crystals by reacting the trans-(±)-4-(4-fluorophenyl)-3-hydroxymethylpiperidine compound with L-tartaric acid to form a salt. The resulting L-tartrate of a trans-(-)-4-(4-fluorophenyl)-3-hydroxymethylpiperidine compound can be isolated and purified by, for instance, separating by such means as filtration, and as occasion demands, washing with the solvent and drying.

The resulting L-tartrate of a trans-(-)-4-(4-fluorophenyl)-3-hydroxymethylpiperidine compound can be suitably used as an intermediate for pharmaceuticals such as paroxetine which is useful, for example, as an antidepressant, as described above.

EXAMPLES

The present invention will be more specifically described by the following examples, without intending to restrict the scope or spirit of the present invention thereto.

Reference Example [Preparation of L-Tartrate of trans-(-)-4-(4-Fluorophenyl)-3-hydroxymethylpiperidine]

A trans-(-)-4-(4-fluorophenyl)-3-hydroxymethylpiperidine monohydrate which was previously optically resolved and desalted was prepared.

Subsequently, 10.00 g (44.0 mmol) of the trans-(-)-4-(4-fluorophenyl)-3-hydroxymethylpiperidine monohydrate, 6.60 g (44.0 mmol) of L-tartaric acid, and 50 ml of methanol were mixed together, and 50 ml of isopropanol was added to the resulting mixture under ice-cooling. The mixture was allowed to stand to precipitate crystals, and the resulting crystals were filtered. The crystals were washed with a 10 ml mixed solvent of 5 ml of methanol and 5 ml of isopropanol and dried, to give 5.60 g (15.6 mmol) of L-tartrate of trans-(-)-4-(4-fluorophenyl)-3-hydroxymethylpiperidine (yield: 35.5%).

The physical properties of the resulting L-tartrate of trans-(-)-4-(4-fluorophenyl)-3-hydroxymethylpiperidine were as follows:

Optical purity [(-)-isomer]: 100.0%
Optical rotation $[\alpha]^{20}_D$: -11.8° (0.5%, water, 100 mm)
Melting point: 161.0° C.
IR (Infrared absorption spectrum): The results are shown in FIG. 1.
Elemental Analysis:
Calculated Value: C, 53.5%; H, 6.2%; N, 3.9%
Found Value: C, 53.3%; H, 6.2%; N, 3.7%

Example 1

There were mixed 10.00 g (47.8 mmol) of trans-(±)-4-(4-fluorophenyl)-3-hydroxymethylpiperidine, 7.17 g (47.8 mmol) of L-tartaric acid, and 50 ml of methanol, and the resulting mixture was then stirred at about 10° C. for four hours and allowed to stand to precipitate the crystals. The precipitated crystals were collected by filtration.

The resulting crystals were washed with 10 ml of methanol, and then dried, to give 5.60 g (15.6 mmol) of L-tartrate of trans-(-)-4-(4-fluorophenyl)-3-hydroxymethylpiperidine (yield: 32.6%).

Figure 2:
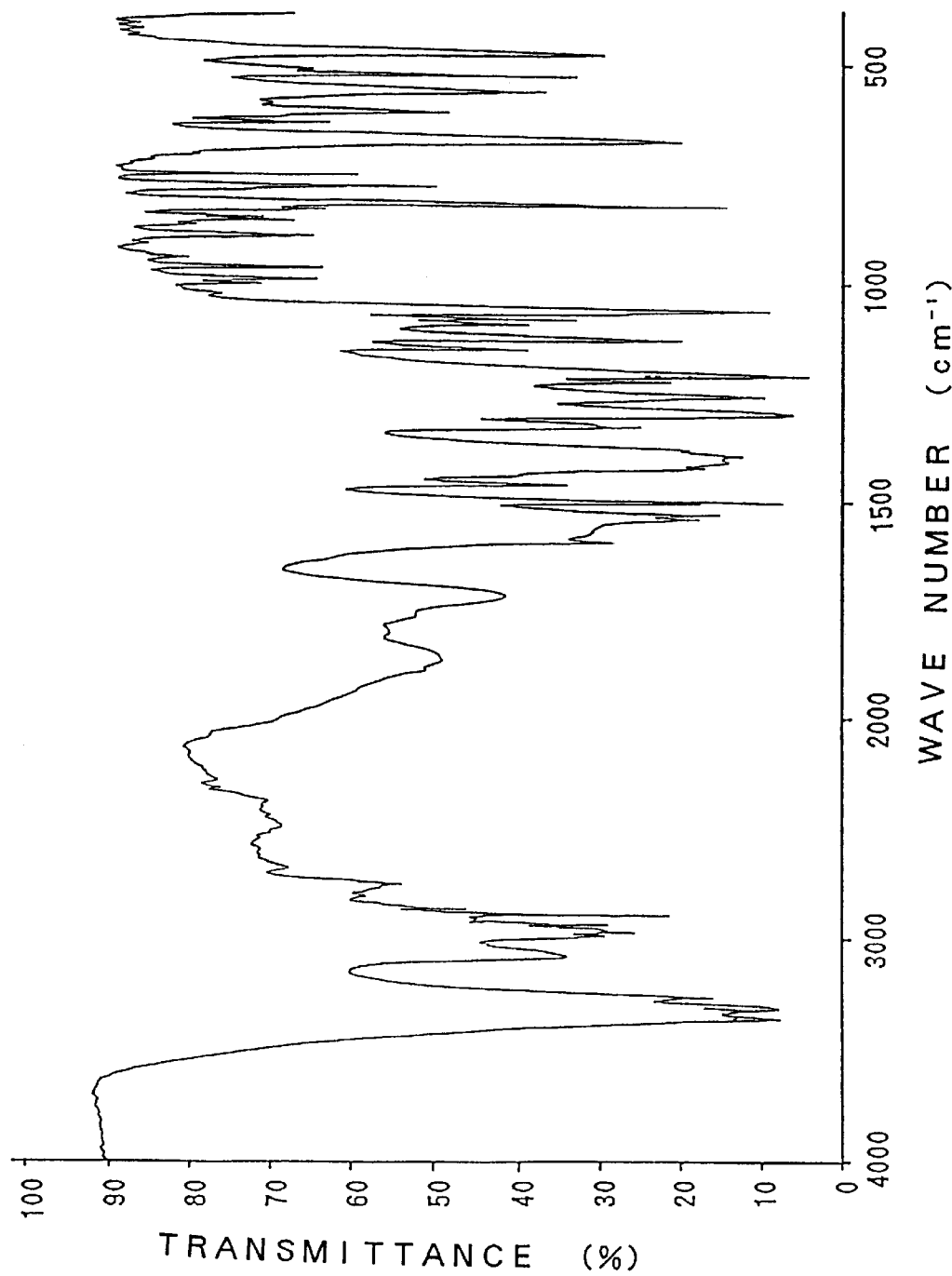
FIG. 2 is a chart showing an infrared absorption spectrum of the L-tartrate of trans-(−)-4-(4-fluorophenyl)-3-hydroxymethylpiperidine prepared in Example 1.

It was confirmed that the resulting compound was L-tartrate of trans-(-)-4-(4-fluorophenyl)-3-hydroxymethylpiperidine from the fact that the infrared absorption spectrum was identified to that of the L-tartrate of trans-(-)-4-(4-fluorophenyl)-3-hydroxymethylpiperidine which has previously been prepared in Reference Example. The infrared absorption spectrum is shown in FIG. 2.

The physical properties of the resulting L-tartrate of trans-(-)-4-(4-fluorophenyl)-3-hydroxymethylpiperidine were as follows:

Optical purity [(-)-isomer]: 98.5%
Optical rotation $[\alpha]^{20}_D$: -12.1° (0.5%, water, 100 mm)
Melting point: 160.9° C.
Bulk density: 680 g/l (measured by graduated cylinder method, the same applied hereinbelow)

Example 2

There were dissolved 10.00 g (47.8 mmol) of trans-(±)-4-(4-fluorophenyl)-3-hydroxymethylpiperidine and 7.17 g (47.8 mmol) of L-tartaric acid in 50 ml of methanol, and 30 ml of acetone was added to the resulting solution. The mixture was then stirred at about 30° C. for four hours and allowed to stand to precipitate the crystals. The precipitated crystals were collected by filtration.

The resulting crystals were washed with 10 ml of a mixed solvent of acetone and methanol (volume ratio of acetone/methanol: 3/5), and then dried, to give 5.37 g (14.9 mmol) of L-tartrate of trans-(-)-4-(4-fluorophenyl)-3-hydroxymethylpiperidine (yield: 31.3%).

Figure 3:
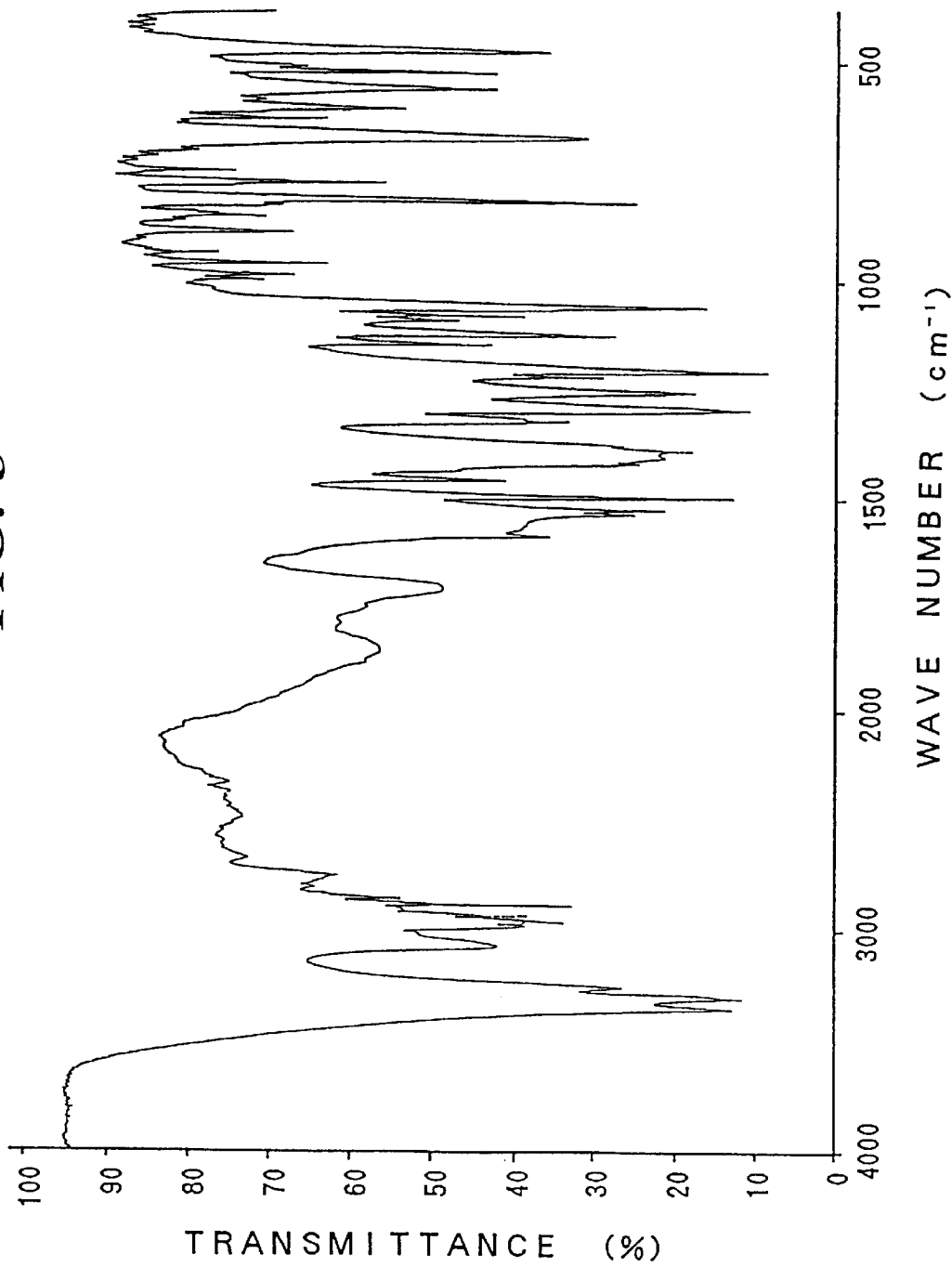
FIG. 3 is a chart showing an infrared absorption spectrum of the L-tartrate of trans-(−)-4-(4-fluorophenyl)-3-hydroxymethylpiperidine prepared in Example 2.

It was confirmed that the resulting compound was L-tartrate of trans-(-)-4-(4-fluorophenyl)-3-hydroxymethylpiperidine from the fact that the infrared absorption spectrum was identified to that of the L-tartrate of trans-(-)-4-(4-fluorophenyl)-3-hydroxymethylpiperidine which has previously been prepared in Reference Example. The infrared absorption spectrum is shown in FIG. 3.

In addition, the physical properties of the resulting L-tartrate of trans-(-)-4-(4-fluorophenyl)-3-hydroxymethylpiperidine were as follows:

Optical purity [(-)-isomer]: 99.5%
Optical rotation $[\alpha]^{20}_D$: -11.7° (0.5%, water, 100 mm)
Melting point: 162.3° C.
Bulk density: 680 g/l Example 3

There were dissolved 10.00 g (47.8 mmol) of trans-(±)-4-(4-fluorophenyl)-3-hydroxymethylpiperidine and 7.17 g (47.8 mmol) of L-tartaric acid in 50 ml of methanol, and 20 ml of isopropanol was added to the resulting solution. The mixture was then stirred at about 20° C. for four hours and allowed to stand to precipitate the crystals. The precipitated crystals were collected by filtration.

The resulting crystals were washed with 10 ml of a mixed solvent of isopropanol and methanol (volume ratio of isopropanol/methanol: 2/5), and then dried, to give 6.53 g (18.2 mmol) of L-tartrate of trans-(-)-4-(4-fluorophenyl)-3-hydroxymethylpiperidine (yield: 38.0%).

Figure 4:
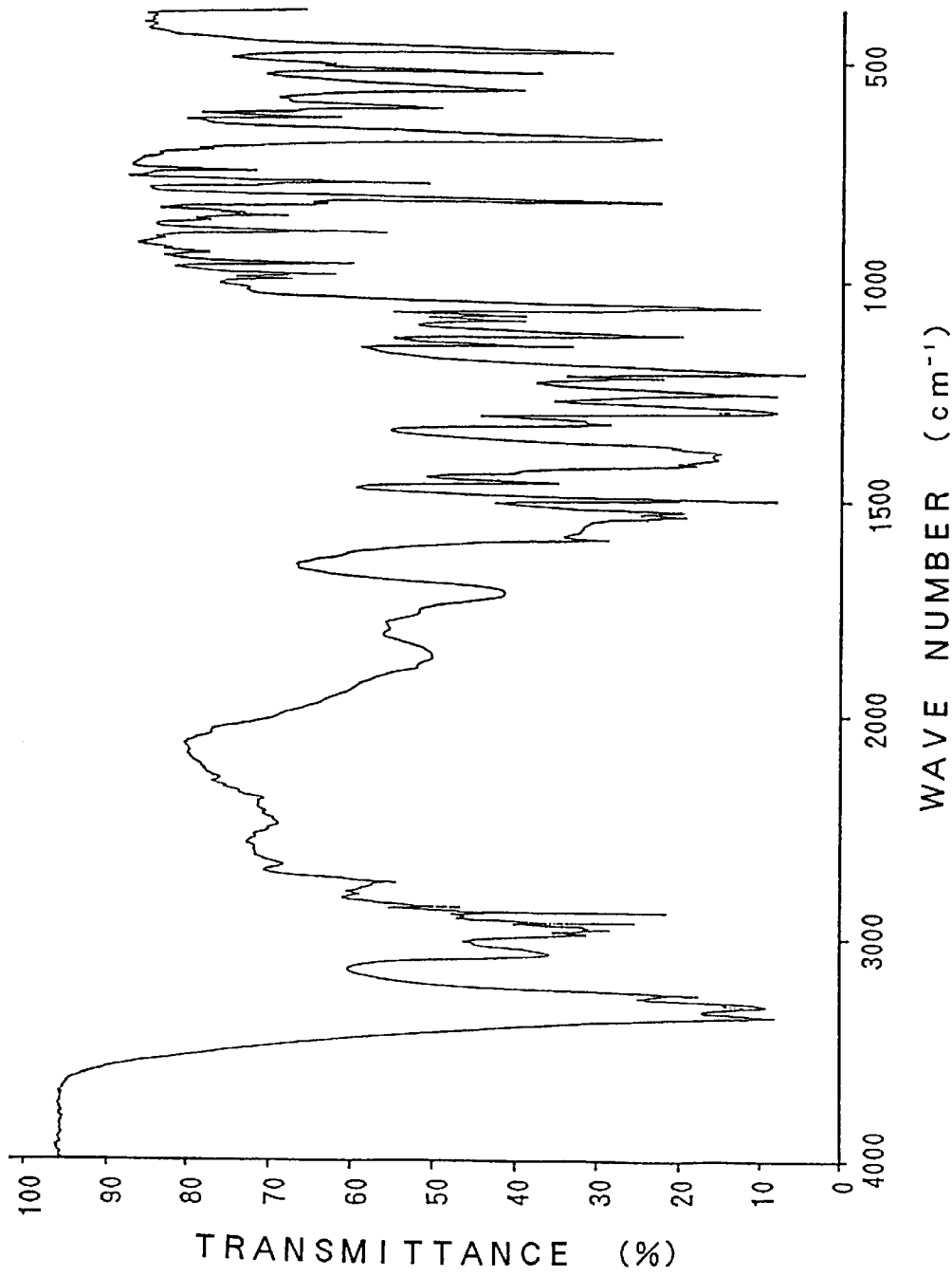
FIG. 4 is a chart showing an infrared absorption spectrum of the L-tartrate of trans-(−)-4-(4-fluorophenyl)-3-hydroxymethylpiperidine prepared in Example 3.

It was confirmed that the resulting compound was L-tartrate of trans-(-)-4-(4-fluorophenyl)-3-hydroxymethylpiperidine from the fact that the infrared absorption spectrum was identified to that of the L-tartrate of trans-(-)-4-(4-fluorophenyl)-3-hydroxymethylpiperidine previously prepared in Reference Example. The infrared absorption spectrum is shown in FIG. 4.

In addition, the physical properties of the resulting L-tartrate of trans-(-)-4-(4-fluorophenyl)-3-hydroxymethylpiperidine were as follows:

Optical purity [(-)-isomer]: 98.2%
Optical rotation $[\alpha]^{20}_D$: -10.6° (0.5%, water, 100 mm)
Melting point: 160.0° C.
Bulk density: 680 g/l Examples 4 and 5

The same procedures as in Example 3 were carried out except that the temperature during stirring was changed from 20° C. to 25° C. (Example 4) or 31° C. (Example 5), respectively, to prepare L-tartrate of trans-(-)-4-(4-fluorophenyl)-3-hydroxymethylpiperidine. As a result, the resulting L-tartrate of trans-(-)-4-(4-fluorophenyl)-3-hydroxymethylpiperidine obtained in Example 4 had optical purity of 99.2%, and yield of 38.6%, and the L-tartrate obtained in Example 5 had an optical purity of 99.9% and yield of 36.4%.

From the above results, it can be seen that according to the processes of Examples 1 to 5, the L-tartrate of trans-(-)-4-(4-fluorophenyl)-3-hydroxymethylpiperidine can be prepared with high production efficiency by using an inexpensive optically resolving agent.

The L-tartrate of trans-(-)-4-(4-fluorophenyl)-3-hydroxymethylpiperidine of the present invention can be suitably used as an intermediate for pharmaceuticals such as paroxetine which is useful, for example, as an antidepressant.

In addition, according to the process of the present invention, the L-tartrate of trans-(-)-4-(4-fluorophenyl)-3-hydroxymethylpiperidine can be prepared with a high production efficiency by using an inexpensive optically resolving agent.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for preparing a trans-(−)-4-(4-fluorophenyl)-3-hydroxymethylpiperidine compound, represented by the formula (I):

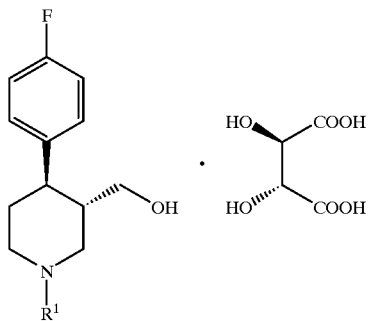

wherein R¹ is hydrogen atom, a substituted or unsubstituted, linear or branched alkyl group having 1 to 6 carbon atoms, or an aralkyl group having 7 to 12 carbon atoms, comprising reacting a trans-(±)-4-(4-fluorophenyl)-3-hydroxymethylpiperidine compound represented by the formula (II):

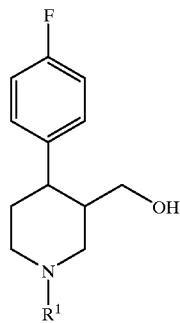

wherein R¹ is the same as defined above, with L-tartaric acid in methanol, or a mixed solvent of methanol and at least one compound selected from the group consisting of isopropyl alcohol and acetone.

2. The process according to claim 1, wherein the amount of at least one compound selected from the group consisting of isopropyl alcohol and acetone is 10 to 500 parts by volume, based on 100 parts by volume of methanol.

3. The process according to claim 1, wherein the amount of methanol or the mixed solvent is 200 to 2000 parts by weight, based on 100 parts by weight of the trans-(±)-4-(4-fluorophenyl)-3-hydroxymethypiperidine compound.

4. The process according to claim 1, wherein the amount of L-tartaric acid is 0.8 to 2 mol per one mol of the trans-(±)-4-(4-fluorophenyl)-3-hydroxymethylpiperidine compound.

5. The process according to claim 1, wherein the temperature during the formation of a salt is 0° to 40° C.

* * * * *